United States Patent [19]

Rys-Cicciari et al.

[11] Patent Number: 5,372,751
[45] Date of Patent: Dec. 13, 1994

[54] ACYL ISETHIONATE SKIN CLEANING COMPOSITIONS CONTAINING BETAINES, AMIDO SULFOSUCCINATES OR COMBINATIONS OF THE TWO

[75] Inventors: Karla J. Rys-Cicciari, Berkel en Rodenrijs, Netherlands; Alan P. Greene, Flemington, N.J.; Frederick S. Osmer, Parsippany, N.J.; Jeanette F. Carque, Verona, N.J.; Robert S. Lee, Spital; Andrew C. Coxon, Bromborough, both of England; Joseph J. Podgorsky, Slate Hill, N.Y.; Mark E. Rerek, Fanwood, N.J.

[73] Assignee: Lever Brothers Company, Division of Conopco, Inc., New York, N.Y.

[21] Appl. No.: 5,717

[22] Filed: Jan. 19, 1993

Related U.S. Application Data

[63] Continuation-in-part of Ser. No. 791,762, Nov. 12, 1991, abandoned, which is a continuation-in-part of Ser. No. 477,682, Feb. 9, 1990, abandoned, and Ser. No. 563,468, Aug. 7, 1990, abandoned.

[51] Int. Cl.$^5$ .................. C11D 17/00; C11D 9/32; C11D 1/12; C11D 15/04
[52] U.S. Cl. .................. 252/554; 252/552; 252/117; 252/557; 252/121; 252/DIG. 5; 252/106; 252/174; 252/DIG. 13; 252/174.21; 252/547; 252/550; 252/545; 252/DIG. 16
[58] Field of Search ........... 252/552, 554, 117, 557, 252/121, DIG. 5, 106, 174, DIG. 13, 174.21, 547, 550, 545, DIG. 16

[56] References Cited

U.S. PATENT DOCUMENTS

| | | |
|---|---|---|
| 3,442,812 | 5/1969 | Barnhurst et al. |
| 3,793,215 | 2/1974 | Smith . |
| 3,879,309 | 4/1975 | Gatti et al. . |
| 3,894,912 | 7/1975 | Geitz . |
| 3,901,832 | 8/1975 | Dugan et al. . |
| 3,950,417 | 4/1976 | Verdicchio et al. . |
| 3,989,647 | 11/1976 | Prince . |
| 4,007,125 | 2/1977 | Prince . |
| 4,137,191 | 1/1979 | Lohr . |
| 4,211,675 | 7/1980 | Machin et al. . |
| 4,234,464 | 11/1980 | Morshauser . |
| 4,335,025 | 6/1982 | Barker et al. . |
| 4,518,517 | 5/1985 | Eigen et al. . |
| 4,749,515 | 6/1988 | Miyamoto . |
| 4,812,253 | 3/1989 | Small et al. . |
| 4,834,970 | 5/1989 | Logi et al. . |
| 4,948,576 | 8/1990 | Verdicchio et al. . |
| 4,954,282 | 9/1990 | Rys et al. . |

FOREIGN PATENT DOCUMENTS

| | | |
|---|---|---|
| 51-1497 | 5/1976 | Japan . |
| 60-8398 | 1/1985 | Japan . |
| 60-161498 | 8/1985 | Japan . |
| 62-141098 | 6/1987 | Japan . |
| 63-225700 | 9/1988 | Japan . |

*Primary Examiner*—Helen M. S. Sneed
*Assistant Examiner*—E. D. Irzinski
*Attorney, Agent, or Firm*—Ronald A. Koatz

[57] ABSTRACT

The present invention relates to solid compositions comprising acyl isethionate and betaines, to compositions comprising acyl isethionate and amidosulfosuccinate, and to compositions comprising acyl isethionate, betaine and amidosulfosuccinate.

26 Claims, No Drawings

ACYL ISETHIONATE SKIN CLEANING COMPOSITIONS CONTAINING BETAINES, AMIDO SULFOSUCCINATES OR COMBINATIONS OF THE TWO

RELATED APPLICATIONS

The subject application is a continuation-in-part of U.S. Ser. No. 791,762, filed Nov. 12, 1991, and now abandoned, which in turn is a continuation-in-part of U.S. Ser. No. 477,682 to Rys et al., filed Feb. 9, 1990, and now abandoned and of U.S. Ser. No. 563,468 to Carque et al., filed Aug. 7, 1990, and now abandoned.

BACKGROUND OF THE INVENTION

1. Field of the Invention

The invention relates to skin cleaning compositions containing major amounts of acyl isethionates in combination with specific mildness enhancing co-actives such as, for example, specific betaines, amido sulfosuccinates, or combinations of the two.

2. Prior Art

Traditionally, soap has been utilized as a skin cleanser. Soap is, however, a very harsh chemical. Irritated and cracked skin result from use of soap, especially in colder climates. There are, however, certain benefits from the use of soap including low cost, ease of manufacture into bars, and good lathering properties.

There has been much commercial activity in attempting to replace soaps with milder surfactants. The introduction of mild synthetic detergent toilet bars, especially those based on sodium cocoyl isethionates, has been particularly successful. Patents relating to this technology include U.S. Pat. No. 2,894,912 (Geitz) disclosing a detergent bar containing 30–70% $C_6$–$C_{18}$ acyl esters of isethionic acid, a suds boosting detergent salt such as 10% alkyl sulfate and 2.5–25% soap.

There appears to be no teaching in the art of a solid detergent bar (one embodiment of the invention) having a specific betaine used in combination with acyl isethionates of specified acyl chain lengths (i.e., greater than 30% $C_{14}$ or lower in a solid detergent bar) and no recognition that the use of betaine in such compositions provides mildness as well as improved lathering properties relative to similar bars with different acyl chain distributions (i.e., 25% or less $C_{14}$ or lower in a solid detergent bar).

In JP 62 141 098, acyl isethionate and carboxy betaine are included in a surfactant base for shampoos and soaps which contain alpha-glucan to impart a smooth feel to skin and hair. There is no mention of acyl chain distribution or of consumer differences (e.g., in lathering) based on such differences.

JP 60 008 398 discusses a similar utility in which dried marmelo fruit seed is used to impart a smooth feel to skin and hair. This reference does not appear to suggest that the isethionate and betaine be used in combination, nor does it suggest that such a combination would have any beneficial effect.

JP 60 161 498 to Shiseido (cited in U.S. Ser. No. 563,468 to Carque et al., filed Aug. 7, 1990) provides an anti-dandruff shampoo with good cleaning and foaming composed of acyl isethionate/lauryl betaine mixtures in a weight ratio of 5:1 to 1:5. There is no teaching of the distribution of the acyl chain length or that the distribution could affect lathering properties of the composition.

JP 62 141 098 to Shiseido (cited in U.S. Ser. No. 563,468 to Carque et al.) teaches shampoo compositions comprising as possible ingredient anionic surfactants such as acyl isethionates and surfactants such as betaine in addition to 0.01–20.0% by weight pullulan. There is no teaching that the two actives should be used together or of the chain distribution of the acyl isethionates. In addition, these compositions are shampoo compositions, not toilet bars.

JP 60 181 200 discusses the use of a propane diol type antibiotics to prevent rancidity and improve perfume stability. Acyl isethionate and betaines are mentioned as possible surfactants for the soap base.

In EP 0,117,135, acyl isethionate and carboxy betaines are included in a surfactant base for shampoos which contain polymers to improve antimicrobial and anti-dandruff efficacy.

JP 7,614,907 discusses the use of betaines in a hard transparent soap formulation. Acyl isethionate may also be included. There is no mention of acyl chain distribution.

JP 63 139 998 discusses a skin detergent blended with clay mineral. Acyl isethionate and betaine are included as possible surfactants. These need not be used together and there is no mention of acyl chain distribution.

U.S. Pat. No. 4,137,191 to Lohr teaches that betaines may be used in combination with anionic surfactants in detergent compositions.

U.S. Pat. No. 3,950,417 to Verdecchi et al. teach betaines may be used with anionic surfactants such as acyl isethionate in detergent compositions.

As indicated above, in none of the above references is it taught to combine acyl isethionate (let alone those having a specific distribution of acyl chain length) and betaines in toilet bar compositions; or is it recognized that this combination may provide both mildness and improved lathering of the bar.

In a second embodiment of the invention, acyl isethionates of defined chain length distribution are used in combination with amido sulfosuccinates.

JP 63 225 700 to Kanebo discloses mild, solid detergent compositions containing acyl isethionate and alkyl sulfosuccinate. The reference does not teach a range of acyl carbon chain lengths from $C_6$–$C_{18}$ or the use of amido sulfosuccinate. The use of amido sulfosuccinates rather than alkyl sulfosuccinates provides unexpected advantages in mildness enhancement.

U.S. Pat. No. 4,007,128 to Prince teaches use of acyl isethionate and $C_{12}$–$C_{14}$ alkanesulfonates. There is no mention of amido sulfosuccinates in the Prince reference.

U.S. Pat. No. 4,749,515 to Miyamoto et al. teaches liquid detergent compositions disclosing use of acylated amido monoesters of sulfosuccinic acid.

U.S. Pat. No. 4,954,282 to Rys et al. is directed to the enhanced mildness observed using stearoyl isethionate relative to cocoyl isethionate. To the extent that the patent shows compositions comprising stearoyl isethionate (and no sulfosuccinate) are significantly milder (relative to a commercially available bar) than compositions comprising cocoyl isethionate (and no sulfosuccinates), a person of ordinary skill in the art would have no expectation whatsoever (and in fact might have the opposite expectation) that addition of sulfosuccinate would enhance the mildness of a composition comprising a cocoyl isethionate to the point where it is significantly milder than a commercially available bar.

U.S. Pat. No. 4,335,025 to Barker discusses synthetic detergent bars containing critical amounts of components. For example, alkali metal salts of $C_{8-16}$ alkyl sulfosuccinate together with a selected water soluble anionic detergent which may include a $C_{10-16}$ acyl isethionate, a waxy extender such as a $C_{12-22}$ fatty acid or alcohol and the like, and other optional extenders. The ratio of surfactant to sulfosuccinate appears to be outside that of this aspect of the invention.

U.S. Pat. No. 3,901,832 to Dugan et al. discusses a detergent bar containing a monoalkyl sulfosuccinate and a specific plasticizer in detergent cakes.

U.S. Pat. No. 3,989,647 to Prince discusses a synthetic toilet bar containing selected amounts of an alkane sulfonate, a fatty acid, and a binder modifier, which may be an alkyl sulfosuccinate.

U.S. Pat. No. 4,812,253 to Small et al. discusses various compositions containing polymeric skin mildness aids, moisturizers, soap and selected surfactants which include acyl isethionates and alkyl sulfosuccinate.

U.S. Pat. No. 4,211,675 to Machin (cited in the European Search Report corresponding to U.S. Serial No. 477,682 to Rys et al., a parent of the subject CIP is directed to detergent bars containing 20–70% acyl ($C_8$–$C_{22}$) isethionates with 5–30% $C_6$–$C_{22}$ sucrose esters to increase slip properties of the bar. Optional ingredients which may be added include dialkyl ($C_6$–$C_9$) sulphosuccinates and monoalkyl ($C_{10}$–$C_{12}$) ethoxylated sulphosuccinates. There is no disclosure of amido sulphosuccinates or of a specific distribution of acyl chain lengths.

U.S. Pat. No. 3,793,215 to Smith (cited in the European Search Report corresponding to U.S. Ser. No. 477,682 to Rys et al., a parent of the subject CIP) discloses detergent bars with a major amount of anhydrous water-soluble higher fatty acid soap and up to 30% synthetic detergent, as a lime soap dispersing agent, including fatty acid amides of sulphosuccinic acid of defined formula. A marked reduction in lime soap curd formation is demonstrated, but varying the amount of synthetic detergent from 0–30% has no significant effect on mildness. There is no disclosure of a bar comprising the synthetic detergent and acyl isethionate and no reference to improving mildness of compositions.

DE-A-3 335 705 (cited in the European Search Report corresponding to U.S. Ser. No. 477,682 to Rys et al., a parent of the subject CIP) discloses a liquid carpet cleaner containing fatty acid ethanolamide sulphosuccinate and sulphonated fatty acid ester. Compared with known cleaners, the composition is said to have various properties improved. The reference is not concerned with mildness of a skin cleaning toilet bar.

None of the references appear to teach the specific combination of isethionate and amido sulfosuccinate taught by this aspect of the invention.

In a third embodiment of the invention, the compositions of the invention comprise acyl isethionate in combination with betaines and amido sulfosuccinates. Bar compositions comprising this combination of actives have been made and shown to be milder than commercially available mild bars. In a preferred aspect of this embodiment of the invention, the betaine and amido sulphosuccinate actives are used in equal parts.

Applicants are unaware of any reference which teaches this specific combination of ingredients or the mildness advantages observable from this specific combination.

Thus it is an object of the invention to provide a skin cleansing composition based on acyl isethionate as a main active in combination with selected betaines, amido sulfosuccinates or, with a combination of both in order to provide mild compositions with good lathering properties.

It is a further object of the invention to provide other coactives (e.g., nonionic alkylpolyglucosides), which may be used with the betaines, sulfosuccinates or combinations of these two coactives.

SUMMARY OF THE INVENTION

In one embodiment of the invention, the invention provides solid skin cleaning compositions comprising:
(i) selected acyl esters of isethionic acid salts in an amount of about 30 to 70%;
(ii) at least one betaine wherein the weight ratio of said acyl esters to betaine is about 8:1 to about 2:1.

In order to provide a composition more acceptable to consumers, the following materials are conveniently used.
(i) free fatty acid in an amount of about 2–40%;
(ii) free isethionate in an amount of about 2–20%; p0 (iii) soap in an amount of about 0–10%;
(iv) free fatty alcohol in an amount 0–10%; and
(v) water in an amount of about 2–20%.

In addition, minor amount of standard miscellaneous ingredients may be used. Examples of such ingredients include $TiO_2$, fragrances & preservatives.

Other coactives may optionally be incorporated in these bars. Such coactives include, for example, nonionic surfactants such as alkylglucosides.

Ultra mild skin cleansing compositions with excellent use properties are provided, based upon acyl esters of isethionate salts as the main active and a betaine as a co-active. Preferred weight ratios of acyl isethionates to betaine are about 8:1 to 2:1 and most preferred to maintain mildness are about 7:1 to 2:1.

In a second embodiment of the invention, the invention provides solid skin cleaning compositions comprising:
(i) acyl esters of isethionic acid salts in an amount of about 30 to 70%;
(ii) at least one amido sulfosuccinate wherein the weight ratio of said acyl esters to amido sulfosuccinate is about 6:1 to about 2:1;
(iii) free fatty acid in an amount of about 2–40%;
(iv) free isethionate in an amount of about 2–20%;
(v) soap in an amount of about 0–10%;
(vi) free fatty alcohol in an amount 0–10%; and
(vii) water in an amount of about 2–20%.

Ultra mild skin cleansing compositions, with excellent use properties are provided, based upon acyl esters of isethionate salts as the main active and amido sulfosuccinate, as a co-active. Preferred weight ratios of acyl isethionates to amido sulfosuccinate are about 6:1 to 2:1 and most preferred to maintain mildness are about 2:1 to 4.5:1.

In a third embodiment of the invention, the invention provides solid skin cleansing compositions which comprise:
(i) selected acyl esters of isethionic acid salts in an amount of about 30 to 70% by weight;
(ii) at least one betaine compound in an amount of about 0.5 to 7.5% by weight of the composition; and
(iii) at least one amido sulfosuccinate compound in an amount of about 1–24% by weight;

wherein the ratio of isethionate to total co-active is from about 6:1 to about 2:1.

In order to provide a composition more acceptable to consumers, the following materials are conveniently used.
(i) free fatty acid in an amount of about 2-40%;
(ii) free isethionate in an amount of about 2-20%;
(iii) soap in an amount of about 0-10%;
(iv) free fatty alcohol in an amount 0-10%;
(v) water in an amount of about 2-20%;

Minor amounts of standard miscellaneous ingredients may also be used. Examples of such include $TiO_2$, fragrances, & preservatives.

The use of acyl isethionates in combination with both betaines and amido sulfosuccinates provides mild skin cleaning compositions while maintaining excellent use (e.g., lathering) properties.

DETAILED DESCRIPTION OF THE INVENTION

In one embodiment of the invention, acyl isethionate actives of defined alkyl chain length distribution (i.e., greater than 30% $C_{14}$ or lower) are used in combination with selected betaine compounds.

According to this embodiment of the invention, the irritancy of the main active, acyl isethionate, can be reduced significantly by the incorporation of these selected betaines.

In addition, surprisingly it has been noted that mildness is obtained while achieving improved lathering ability. Specifically, lathering in a bar is improved when using betaine in combination with an acyl isethionate having a chain distribution greater than 30% $C_{14}$ or lower in that bar relative to acyl isethionates having a chain distribution of less than 25% $C_{14}$ or lower in a bar.

The cleansers resulting from this mixture of actives have superior skin mildness, excellent lather and good tactile characteristics. In addition, they are easily processable using standard manufacturing equipment.

Isethionate salts in the range of about $C_6$–$C_{18}$, such as those derived from coconut fatty acids, for example, have been employed in a number of commercial cleansing products and are known to produce a voluminous, creamy lather. This active, by itself, has been shown to be very mild to the skin. These actives are solid at room temperature and serve as excellent structurants when used in bar formulations.

The isethionate ester salts that may be employed herein are preferably acyl ester isethionates and most preferably the cocoyl ester. These preferred esters may be prepared from the usual cocoyl fatty acids having a small percentage of fatty acid chains below $C_8$ with over 95% of the carbon chain distribution being between $C_8$ and $C_{18}$ and more than half being $C_{12}$ or less. A typical cocoyl fraction will contain the chain length distribution in Table 1.

TABLE 1

| Chain Length | Wt. % Fatty Acid Combined As Cocoyl Isethionate |
|---|---|
| $C_{6-10}$ | 10-25 |
| $C_{12}$ | 45-55 |
| $C_{14-18}$ | 20-40 |
| $C_{18}$ unsaturated | 1-15 |

It is desirable for such isethionate based esters to be combined with selected betaines to provide mildness to the skin together with good bar properties such as good lather volume.

Betaines and amidobetaines are both known to be mildness enhancing agents. The cocamidobetaine, in particular, has good lather properties.

Skin testing and use property evaluation have shown that the preferred ratio of isethionate to betaines, according to this aspect of the invention, is 2:1 to 8:1 or even as high as 10:1, preferably from about 2:1 to about 7:1, optimally about 4.5:1.

The betaines useful with this embodiment of the invention may be any suitable betaine, either carboxybetaine or sulfobetaine with the following structure (I):

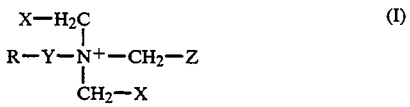

where R is any hydrocarbon chain distribution at least about 90% $C_5$-$C_{17}$; X is either a single hydrogen, H, or of the form $CH_2OH$; Y is either a methyl linkage, $CH_2$, or of the form $CONHCH_2CH_2CH_2$ (amidopropyl betaine); Z is either a carboxyl group, $COO^-$ (carboxybetaine), or of the form $CHOHCH_2SO_3$— (sulfobetaine or hydroxy sultaine); provided that when X, Y and Z are respectively H, $CH_2$ and $COO^-$ in combination, R is less than 50% $C_{15}$-$C_{17}$.

Preferably to insure processability, mildness and other use properties the betaine is an amidopropyl betaine.

Specific betaines useful in this embodiment of the invention are lauryl betaine (Varion CDG from Sherex), cocamidopropyl betaine (Varion CADG from Sherex), coco betaine (Mackam CB from Mcintyre), cocamidopropyl hydroxy sultaine (Varion CAS from Sherex) and tallow dihydroxyethyl glycinate (Varion TEG from Sherex).

The most preferable betaines are Cocamidopropyl Betaine of the Structure II:

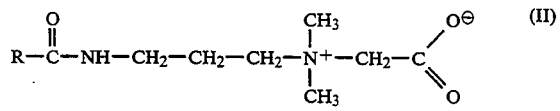

R is Structure II is derived from coconut fatty acids, but in other forms may be any convenient alkyl group. The chain length distribution of coconut fatty acids is similar to that for the coco group on the isethionate. The chain length distribution will contain at least 90% of $C_8$ to $C_{18}$ with more than half made up of $C_8$ to $C_{14}$. A typical fatty acid distribution in the cocoyl portion is the same as in Table 1.

As previously noted, soap may be somewhat harsh and when present in the compositions of this aspect of the invention should be at a level no higher than about 35%, preferably less than 5%, and advantageously totally absent.

Free fatty acids of about 8-22 carbon atoms are desirably incorporated within the compositions of the present invention. Some of these fatty acids are present to operate as superfatty agents and others as skin feel and creaminess enhancers. Fatty alcohols, fatty amides and the like may also be employed. Superfatting agents enhance lathering properties and may be selected from fatty acids of carbon atoms numbering 8–18, preferably 10–18, in an amount up to 40% by weight of the composition. Skin feel and creaminess enhancers, the most important of which is stearic acid, are also desirably present in these compositions.

Other performance chemicals and adjuncts may be needed or employed with these compositions. The amount of these chemicals and adjuncts may range from about 0% to about 20% by weight of the total compositions. For instance, there may be included humectants such as glycerin; anti wear agents such as polymer JR$^{(R)}$ and natural and synthetic gums and the like; germicides, perfumes, colorants, dyes, pigments such as titanium dioxide, electrolytes, and water.

In a second embodiment of the invention, acyl isethionate actives are used in combination with selected amido sulfosuccinate compounds.

According to this second embodiment of the invention, the irritancy of the main active, acyl isethionate, can be reduced significantly by the incorporation of selected amido sulfosuccinates.

The cleansers resulting from this mixture of actives have superior skin mildness, excellent lather, low bar mush values and good tactile characteristics. In addition, they are easily processable using standard manufacturing equipment.

Isethionate salts in the range of about $C_6$–$C_{18}$, such as those derived from coconut fatty acids, for example, have been employed in a number of commercial cleansing products and are known to produce a voluminous, creamy lather. This active, by itself, has been shown to be mild to the skin. These actives are solid at room temperature and serve as excellent structurants when used in bar formulations.

The isethionate ester salts that may be employed according to this aspect of the invention are preferably acyl ester isethionates and most preferably the cocoyl ester. These preferred esters may be prepared from the usual cocoyl fatty acids having a small percentage of fatty acid chains below $C_8$ with over 95% of the carbon chain distribution being between $C_8$ and $C_{18}$ and more than half being $C_{12}$ or less. A typical cocoyl fraction will contain:

| Chain Length | Wt. % Fatty Acid Combined As Cocoyl Isethionate |
|---|---|
| $C_{6-10}$ | 10–25 |
| $C_{12}$ | 45–55 |
| $C_{14-18}$ | 20–40 |
| $C_{18}$ unsaturated | 1–15 |

It is desirable for such isethionate based esters to be combined with selected amido sulfosuccinates to provide mildness to the skin together with good bar properties such as processability, low mush, and good lather.

Alkali metal salts of sulfosuccinate monoesters and mono alkyl amido sulfosuccinate monoesters and in particular those derived from coco-monoethanolamides, are known to be mild to both skin and eyes. The coco monoethanolamide sulfosuccinate salts, in particular, have good lather properties.

In U.S. Pat. No. 4,954,202 to Rys et al., the available data showed that bar formulations containing stearoyl isethionate (with or without amido sulfosuccinate) were surprisingly milder relative to a formulation containing cocoyl isethionate. No examples were shown using a combination of cocoyl isethionate and amido sulfosuccinate but, given the mildness of stearoyl versus cocoyl, it would not have been expected that the addition of amido sulfosuccinate to cocoyl would enhance mildness to the levels of the stearoyl/amido sulfosuccinate combination. Skin testing and use property evaluation have shown that the preferred ratio of isethionate to amido sulfosuccinate is 2:1 to 6:1.

Examples have shown that increasing the amount of amido sulfosuccinate (i.e., moving closer to the 2:1 ratio) increases the mildness (i.e., as measured statistically by p values which are defined more specifically below) of the bar composition (see example 6 where, as percentage of amido sulfosuccinates increases in compositions 13 to 12 to 11, p value decreases (indicating increased mildness). By contrast, since a 4:1 ratio of isethionate to alkyl sulfosuccinate shows equivalence to a commercial mild bar and a ratio of 1:1 isethionate to alkyl isethionate shows a bar which is less mild than the same commercially mild bar (see example 7) the trend indicates that increasing the percentage of alkyl sulfosuccinate (as opposed to amido sulfosuccinate) results in decreased mildness. Since increasing amido sulfosuccinate increases mildness while increasing alkyl sulfosuccinate decreases mildness, together these trends show that amido sulfosuccinate is milder than alkyl sulfosuccinate over a broad range of values.

In general, p value is defined as the probability that two numbers are different due to chance rather than that they really are different. The lower the p value, the less likely that they are equal due to chance and the more likely that they are different. Thus a p value of 0.10 indicates that there is a 10% chance that observed differences are random coincidence and a 90% chance that the difference is based on a real difference.

The amido sulfosuccinates useful with this embodiment invention may be any suitable sulfosuccinate either mono-esters (half esters) or di-esters and any alkali metal, alkaline earth metal or ammonium salt, but the sulfosuccinates are preferably monoesters and preferably prepared through an alkanolamine intermediate so as to introduce an amido group into the molecule. Preferably to insure processability, mildness and other use properties the sulfosuccinate monoester is prepared through a monoethanolamide intermediate.

The most preferable sulfosuccinates are, Disodium Cocamido Monoethanolamide Sulfosuccinate of the Structure 1:

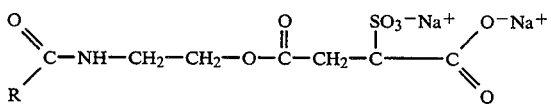

R in Structure 1 is derived from coconut fatty acids, but in other forms may be any convenient alkyl group. The chain length distribution of coconut fatty acids is similar to that for the coco group on the isethionate. The chain length distribution will contain at least 90% of $C_8$ to $C_{18}$ with more than half made up of $C_8$ to $C_{14}$. A typical fatty acid distribution in the cocoyl portion is as follows:

| Chain Length | Wt. % Fatty Acid Combined As Cocoyl Amido Sulfosuccinate |
|---|---|
| $C_{6-10}$ | 10–25 |
| $C_{12}$ | 45–55 |
| $C_{14-18}$ | 20–40 |

-continued

| Chain Length | Wt. % Fatty Acid Combined As Cocoyl Amido Sulfosuccinate |
|---|---|
| $C_{18}$ unsaturated | 1–15 |

The sulfosuccinate of Structure 1 may conveniently be prepared by a two step reaction:
1. An ester condensation reaction of Coco alkanolamide with Maleic Anhydride.
2. Sulfonation of the double bond with Sodium Sulfite as described below.

Preparation of Disodium Cocamido Monoethanolamide Sulfosuccinate a) preparation of the coco-fatty ethanolamide

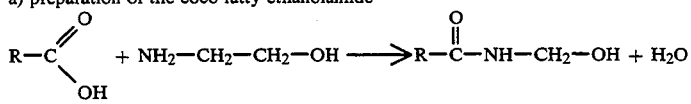

coco fatty acid + ethanol amine ⟶ coco fatty ethanolamide + water b) ester condensation reaction of maleic anhydride and the coco ethanolamide

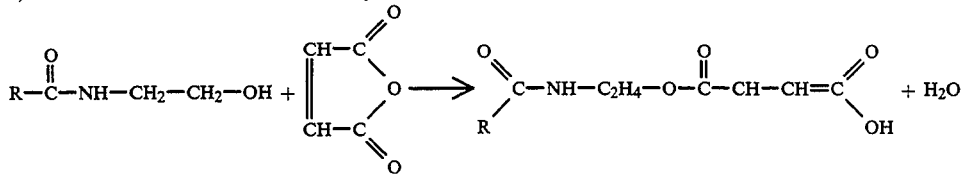

coco fatty ethanolamide + maleic anhdydride (molar excess) $\xrightarrow[\substack{2.\ \text{catalyst} \\ 3.\ 2\ \text{hours}}]{1.\ 70\text{–}100°\ C.}$ monoester + water c) sulfonation with sodium sulfite
(See Step b) + $Na_2SO_3$                                                                                   (Structure 1)

monoester + sodium sulfite $\xrightarrow[\text{solution}]{\text{aqueous}}$ disodium cocamido mea sulfosuccinate The relative amounts of isethionate esters to sulfosuccinate will range in the weight ratio of about 2:1 to 4.5:1, or even as high as 6:1, preferably from about 3:1 to about 4:1, optimally about 3.5:1.

As previously noted, soap may be somewhat harsh and when present in the compositions of this invention should be at a level no higher than about 25%, preferably less than 5%, and advantageously totally absent.

Free fatty acids of about 8–22 carbon atoms are desirably incorporated within the compositions of this embodiment of the invention. Some of these fatty acids are present to operate as superfatting agents and others as skin feel and creaminess enhancers. Fatty alcohols, fatty amides and the like may also be employed. Superfatting agents enhance lathering properties and may be selected from fatty acids of carbon atoms numbering 8–18, preferably 10–18, in an amount up to 40% by weight of the composition. Skin feel and creaminess enhancers, the most important of which are stearic acid and cetyl alcohol, are also desirably present in these compositions.

Other performance chemicals and adjuncts may be needed or employed with these compositions. The amount of these chemicals and adjuncts may range from about 0% to about 5% by weight of the total compositions. For instance, there may be included humectants such as glycerin; anti wear agents such as polymer JR and natural and synthetic gums and the like; germicides, perfumes, colorants, dyes, pigments such as titanium dioxide, electrolytes, and water.

In a third embodiment of the invention, acyl isethionate actives are used in combination with both betaines and amido sulfosuccinates.

According to this embodiment of the invention, any of the betaines described above may be used in combination with any of the amido sulfosuccinates also described above. The ratio of isethionate to total co-active (i.e., betaines plus sulfosuccinates) should be from 2:1 to 6:1.

In a preferred aspect of this embodiment of the invention, the coactives are used in about equal amounts since this ratio was shown to have tremendous significance in mildness (as measured by p-values) even relative to ratios of betaine to sulfosuccinate of 6:1 or 1:6.

Evaluation of an active's skin mildness properties are determined through the following test procedure.

The Flex Wash

Each of the products' skin mildness properties were evaluated in a paired comparison with a control product using a standardized Flex Wash test. The Flex Wash test procedure consists of three daily two minute washes of the anticubital fossa (flex area of elbow). This method is an "exaggerated use" method designed to differentiate very mild products. Erythemal response varies only slightly with temperature and humidity fluctuations making the protocol suitable for year round testing.

Approximately 15–20 panelists were used as the test population. Panelist flex areas must be free of any skin condition (eczema, dryness, irritation, cuts or abrasions). Anyone taking antihistamines, anti-inflammatory drugs (more than 8 per week) or topical, oral or injectable cortisone on a regular basis was excluded from the study. The panel was divided into two sub-groups which were balanced for left handedness. Group I was assigned composition "A" for the left flex and "B" for the right flex. Group II reversed the order.

Following an evaluation, the panelist was instructed to moisten the left flex area, the sponge and test compositions formulated as toilet bars were dampened with tap water (100 ppm calcium/magnesium ions). The sponge was then stroked over the test bar 10 times by the evaluator. The "dosed" sponge was placed in the panelist's right hand. The panelist then washed the left flex area for exactly two minutes. Thereupon, the flex was rinsed and patted dry. This washing procedure was repeated on the right arm with appropriate composition. Thus, both arms are tested simultaneously. Washing by this procedure was repeated three times daily for 5 consecutive days for a total of 15 washes. Treatment times were scheduled 1.5 hours apart. Each test site was evaluated immediately prior to washing and 4 hours after the third daily wash. A slightly different procedure was used for Example 7. In this evaluation, the flex area was only washed for one minute, repeated four times daily for five consecutive days for a total of 20 washes. The test site was evaluated immediately prior to each wash.

One trained assessor evaluated test sites for a total of 20 evaluations. The grading scale was as follows:

0—no erythema
0.5—barely perceptible erythema
1—mild spotty erythema/no edema
1.5—mild/moderate erythema/with or without edema
2—moderate confluent erythema/with or without edema or vesiculation Each test site was treated in the prescribed method until a grading of "2" or greater was attained or 15 washings had been completed. When a score of "2" or greater was attained, the treatment was discontinued on that flex. The final score was then carried through for all remaining evaluations. The remaining flex was washed until either a grading of a least "2" or 15 treatments were attained, whichever was first. In the Examples of this specification, the final grading, Mean Rank Scores, is the sum total of grade scores for 15 assessments per panelist averaged over the scores from all panelists. Thus, theoretically, the average score could range from 0 to 30; the lower score indicating absolutely no skin irritation while the 30 score being the most severe. Mean Endpoint Erythema scores are the mean of the evaluation scores, for each panelist, at which the first arm received a grade of "2" or greater erythema score or at the completion of fifteen washes. The Mean Rank Erythema scores are analyzed and compared using the Wilcoxon Signed Rank Test (two-sample).

II Description of Patch Test & Results

This test is employed to screen formulations for the more extensive flex wash. In a patch test, up to six formulations can be tested at the same time on each subject, using occluded patches which remain on the forearm for 24 hours. Test sites are evaluated at 4 and 24 hours following the removal of the patches for erythema and dryness. Scores range from 0 to 2 in increments of half point and are graded as per the flex wash.

The following examples will more fully illustrate the embodiments of this invention. All parts, percentages and proportions referred to herein and in the appended claims are by weight of the total Composition unless otherwise stated.

In the examples below, skin mildness properties were evaluated by comparison to one of the following control formulations:

TABLE I

Control Formulations

| Component | % in Formulation A | % in Formulation B |
|---|---|---|
| Na Cocoyl Isethionate | 68.3 | 49.8 |
| Free Fatty Acid | 19.2 | 23.3 |
| Soap | — | 8.3 |
| Na Alkylbenzene Sulfonate | — | 2.0 |
| Na Isethionate | 6.5 | 4.7 |
| Sodium Stearate | — | 3.0 |
| Miscellaneous | 1.0 | 3.6 |
| Water | 5.0 | 5.3 |

Control formulations A and B are commercially available bars which have been shown to be similar in mildness in the Flex Wash Test. Therefore, a comparison of the following embodiments of the invention with A or B will provide comparable magnitude estimates of mildness in the following examples. The criteria of mildness for this invention is significant increase in mildness at 90% confidence, or better (P-value $<0.10$). It should be noted that the selection of 90% confidence is somewhat arbitrary and that results of even 80% can be considered significant and certainly show directional significance in any event.

As indicated above, p value is defined as the probability that two numbers are different due to chance rather than that they really are different. The lower the p value, the less likely that they are equal due to chance and the more likely that they are different. Thus a p value of 0.10 indicates that there is a 10% chance that observed differences are random coincidence and a 90% chance that the difference is based on a real difference.

EXAMPLE 1

This example illustrates the mildness of acyl isethionate/betaine combinations. The effect of acyl isethionate/betaine ratio is examined. Table II gives the formulations and Table III gives the Flex Wash results.

TABLE II

| Component | % in Formulation 1 | % in Formulation 2 | % in Formulation 3 | % in Formulation 4 |
|---|---|---|---|---|
| Sodium Cocoyl Isethionate | 53.7 | 57.8 | 46.5 | 63.1 |
| Lauryl Betaine | 18.7 | 13.4 | — | — |
| Cocaimidopropylbetaine | — | — | 7.4 | 6.3 |
| Free Fatty Acid | 15.1 | 16.3 | 32.76 | 17.8 |
| Sodium Isethionate | 5.0 | 5.5 | 8.2 | 6.0 |
| Sodium Chloride | 1.2 | 0.8 | 1.4 | 1.0 |
| Water | 5.5 | 5.3 | 5.0 | 4.9 |
| Miscellaneous | 0.8 | 0.8 | — | 0.9 |
| Cocoyl Isethionate/Betaine Ratio | 2.9/1 | 4.3/1 | 6.3/1 | 10.0/1 |

TABLE III

| Formulation | Control | Mean Scores Endpoint Erythema Formulation | Mean Scores Endpoint Erythema Control | Mean Rank Scores Erythema Formulation | Mean Rank Scores Erythema Control | P-Value |
|---|---|---|---|---|---|---|
| 1 | A | 0.8 | 2.0 | 10.7 | 26.37 | 0.0000 |
| 2 | A | 1.3 | 1.9 | 12.3 | 24.7 | 0.0002 |
| 3 | B | 1.0 | 1.6 | 12.9 | 22.1 | 0.0051 |
| 4 | A | 1.5 | 1.3 | 21.7 | 17.3 | 0.202 |

Formulations 1, 2, and 3 are significantly milder than the controls. Formulation 4 is not significantly milder than the control and shows that the critical ratio of acyl isethionate to betaine (i.e., ratio at which enhanced mildness results are no longer observed) is somewhere between 6.5 (formulation 3) and 10. As seen in formulation 5 (example 2) which follows, the critical ratio is assumed to be about 8.

EXAMPLE 2

Superior mildness is demonstrated for the following cocoyl isethionate/betaine examples, where the betaine is tallow dihydroxyethyl glycinate (Formulation 5). The cocoyl isethionate to betaine ratio is 7.8:1 for this formulation.

| Component | Formulation 5 |
|---|---|
| Na Cocoyl Isethionate | 60.6 |
| Tallow Dihydroxyethyl-Glycinate | 7.8 |
| Stearic Acid | 13.4 |
| Coco Fatty Acid | 3.7 |
| Na Isethionate | 5.7 |
| Sodium Chloride | 1.2 |
| Miscellaneous | 0.9 |
| Water | 6.7 |

TABLE IV

FLEX WASH

| | | Mean Endpoint Erythema | | Mean Rank Scores | | |
|---|---|---|---|---|---|---|
| Formulation | Control | Formulation | Control | Formulation | Control | P-Value |
| 5 | A | 1.2 | 1.5 | 10.7 | 16.3 | 0.056 |

This flex wash test demonstrates that the indicated betaine can be used in combination with isethionate to obtain enhanced mildness within statistically significant values (i.e., p value <0.10).

EXAMPLE 3

Lather Volume measurements were performed on the forementioned formulations. A brief description of the lather test is reported below.

Objective Lather Volume—This test involved rotating the toilet bar 15 half turns under running 95° F. water. The bar was then set aside and the resulting lather was worked by hand for 10 seconds. A measuring funnel was then placed over the hands and both were lowered into a sink filled with water to the 0 ml mark on the measuring funnel. When the hands were fully immersed, they were removed from beneath the funnel. The funnel was then lowered to the bottom of the sink and lather volume was measured.

Example 3 illustrates the lather volume generated by each formulation of this invention. Each product produces a good lather volume, very close to control B, a commecially available good lathering bar.

TABLE V

| Formulation | Acyl Isethionate:Betaine Ratio | Lather Volume (ml) |
|---|---|---|
| B | — | 105 |
| 1 | 2.9/1 | 92 |
| 2 | 4.3/1 | 98 |
| 3 | 6.3/1 | 93 |
| 4 | 10.0/1 | 101 |

EXAMPLE 4

The following compositions 6 & 7 were tested using the lather test described in example 3 above to determine whether there is a difference between the use of 25% or less $C_{14}$ or lower isethionate in a bar compared to 30% or higher $C_{14}$ or lower in a bar:

| Component | 6 | 7 | 8 |
|---|---|---|---|
| CAPRIC/CAPRYLIC ISETHIONATE | 5.00 | 6.20 | 8.0 |
| LAURIC ISETHIONATE | 14.00 | 16.50 | 21.5 |
| MYRISTIC ISETHIONATE | 6.00 | 7.3 | 10.0 |
| PALMITIC ISETHIONATE | 13.75 | 11.0 | 6.0 |
| STEARIC ISETHIONATE | 11.25 | 9.0 | 4.0 |
| CAPRIC/CAPRYLIC ACID | 1.68 | 2.08 | — |
| LAURIC ACID | 4.86 | 5.73 | — |
| MYRISTIC ACID | 2.36 | 2.88 | — |
| PALMITIC ACID | 10.87 | 9.86 | 16.3 |
| STEARIC ACID | 9.57 | 8.76 | 13.3 |
| COCAMIDOPROPYLBETAINE | 7.50 | 7.50 | 7.5 |
| WATER | 5.00 | 5.0 | 5.0 |
| SODIUM CHLORIDE | 1.21 | 1.21 | 1.21 |
| SODIUM ISETHIONATE | 6.94 | 6.92 | 6.71 |
| Lather volume (ml) | 77.2 | 83.6 | 88.1 |

Eighteen individual trials were run and composition of bar 7 (30% $C_{14}$ or lower) had a higher lather (i.e., 83.6 lather volume) than the composition of bar 6 (25% $C_{14}$ or lower).

A Duncan's Multiple Range test (an ASTM approved test for measuring values) was run and demonstrated a real difference ($p<0.05$) between the lather generated by each of the bars. This clearly shows a critical difference in lather value based on acyl chain length distribution.

Moreover, when a further bar composition (composition 8) having 36% $C_{14}$ or lower was tested, lather volume was found to be 88.1, again clearly distinct from composition 6 with no more than 25% $C_{14}$ (as well as being statistically different than compositions having no more than 30% $C_{14}$, i.e., composition 7).

Examples 5–9 relate to the second embodiment of the invention, i.e., cocoyl isethionate in combination with amido sulfosuccinate.

EXAMPLE 5

Formulation 9 & 10 were prepared and compared to formulation B in Table I above, i.e., a commercially sold cocoyl isethionate formulation containing soap and other ingredients. Formulations 9 and 10 are set forth below:

| Component | Formulation (All Percentages by Weight) | |
|---|---|---|
| | 9 | 10 |
| Sodium cocoyl isethionate | 45.5 | 46.2 |
| Free fatty acid | 32.7 | 33.1 |
| Sodium isethionate | 3.9 | 2.6 |
| Disodium cocamido MEA sulfosuccinate | — | 11.7 |
| Sodium lauroylsulfosuccinate | 11.5 | — |
| Sodium chloride | 0.35 | 0.35 |
| Titanium dioxide | 0.5 | 0.5 |
| Perfume | 1.0 | 1.0 |
| Water | 4.5 | 4.5 |
| EDTA* | 0.02 | 0.02 |
| EHDP* | 0.02 | 0.02 |

*preservatives

Table VI below lists mildness results based on the comparisons of formulations 9 and 10 with composition B in a flex wash test:

TABLE VI

| Formulation | Control | Mean Scores Endpoint Erythema | | Mean Rank Scores Erythema | | P-Value |
|---|---|---|---|---|---|---|
| | | Formulation | Control | Formulation | Control | |
| 9 | B | 1.4 | 1.4 | 17.94 | 19.06 | 0.7572 |
| 10 | B | 0.9 | 1.6 | 12.56 | 22.44 | 0.0027 |

This example shows that formulation 10 (with amido sulfosuccinate) is significantly milder than the composition B while formulation 9 (with alkyl sulfosuccinate) was statistically equal. Thus, the amido sulfosuccinate is clearly superior to the alkyl sulfosuccinate.

To further show that amido sulfosuccinate could be expected to be milder than alkyl sulfosuccinate over a broad range of values, applicants tested a commercially available bar (Eucerin$_{TM}$) having an approximately 1:1 ratio of sodium cocoylisethionate to alkyl sulfosuccinate (disodium lauryl sulfosuccinate) and tested against commercial bar B and found that the commercial bar was significantly milder (p=0.002).

Since applicants have previously shown (see U.S. Pat. No. 4,954,282 to Rys et al. hereby incorporated by reference) that a ratio of 4:1 isethionate to alkyl sulfosuccinate establishes equivalence with commercial bar B, it can be seen that increasing alkyl sulfosuccinate decreases mildness.

Further, as seen in Example 7 below, increasing the amount of amido sulfusuccinate (decreasing ratio of isethionate to amido sulfosuccinate) increases mildness.

Thus, since increasing alkyl sulfoccinate decreases mildness while increasing amido sulfosuccinate increases mildness, these trends together indicate that amido sulfosuccinate can be expected to be milder than alkyl sulfosuccinate over a broad range of values.

EXAMPLE 6

This Example illustrates the unexpected mildness of the sodium cocoyl isethionate/disodium cocamido MEA sulfosuccinate combination. Table VII lists compositions and Tables VIII and IX list mildness results from Flex Wash and Patch Tests, respectively.

TABLE VII

| Ingredient | Formulation | | | |
|---|---|---|---|---|
| | 11 | 12 | 13 | 14 |
| Sodium Cocoyl Isethionate | — | — | 40.0 | 33.10 |
| Sodium Stearoyl Isethionate | 40.00 | 33.10 | — | — |
| Disodium Cocamido MEA Sulfosuccinate | — | 15.0 | — | 15.0 |
| Free Fatty Acid | 36.0 | 29.8 | 36.0 | 29.8 |
| Sodium Isethionate | 11.0 | 9.1 | 11.0 | 9.1 |
| Perfume | 1.0 | 1.0 | 1.0 | 1.0 |
| Titanium Dioxide | 0.2 | 0.2 | 0.2 | 0.2 |
| Water | 10.0 | 10.0 | 10.0 | 10.0 |
| Miscellaneous | 1.8 | 1.8 | 1.8 | 1.8 |

Each of these formulations was compared to control formulation B in Table I.

Table VIII below lists mildness results based on the comparisons of the formulations with control formulation B in a flex wash test:

TABLE VIII

| Formulation | Control | Mean Scores Endpoint Erythema | | Mean Rank Scores Erythema | | P-Value |
|---|---|---|---|---|---|---|
| | | Formulation | Control | Formulation | Control | |
| 11 | B | 0.57 | 1.5 | 9.53 | 21.47 | 0.0001 |
| 12 | B | 0.62 | 1.19 | 10.08 | 16.92 | 0.015 |
| 13 | B | 0.95 | 1.09 | 12.72 | 12.83 | 0.64 |
| 14 | B | 0.79 | 1.74 | 10.79 | 24.21 | 0.0002 |

Table IX lists mildness results based on comparisons of formula 11 versus 13 and 13 versus B formulations in a patch test.

TABLE IX

| Formulation | Control | Patch Score (24 hours) | | P-Value |
|---|---|---|---|---|
| | | Formulation | Control | |
| 11 | 13 | 1.92 | 10.38 | <0.10 |
| 13 | B | 10.38 | 6.92 | >0.10 |

As can be seen from the data above, and as is already known from U.S. Pat. No. 4,954,282 to Rys et al., the use of a formulation containing stearoyl isethionate (i.e., formulation 11 in Table VII above) is surprisingly milder relative to a formulation containing cocoyl isethionate (i.e., formulation 13 in Table VII above). This is confirmed by the flex wash test in Table VIII where formulation 11 has a p-Value of 0.0001 (significantly milder) relative to a commercially available mild bar B while formulation 13, the cocoyl isethionate composition, has a p-Value of 0.64 (not significantly milder).

Formulation 12 is similar to formulation 11 except that it has 15% cocamido sulfosuccinate and, given the mildness enhancement using a stearoyl isethionate in place of cocoyl isethionate, one of ordinary skill might expect the combination of the active stearoyl isethionate and the amido sulfosuccinate coactive to also be mild relative to composition B. This is confirmed in Table VIII where formulation 12 has a p-Value of 0.015 (significantly milder) relative to composition B.

Similarly, given the fact that composition 13 was not more mild relative to composition B, a person of ordinary skill in the art would expect a composition comprising cocoyl isethionate and an amido sulfosuccinate coactive (i.e., formulation 14) also to be not significantly milder relative to commercial bar B or, if milder at all, in a non-statistically significant way.

Surprisingly, however (as seen in Table VIII) when formulation 14 was compared to formulation B, it has a P-Value of 0.0002 which showed that the bar was significantly milder relative to bar B.

The patch test in Table IX again shows that formulation 11 (containing stearoyl isethionate) is significantly milder than formulation 13 (containing cocoyl isethionate) but that the formulation 13 is not statistically milder than a commercially available mild bar B. Thus, the fact that formulation 14 (which contains cocoyl isethionate active and amido sulfosuccinate coactive) is anywhere close to formulation 11 in mildness (as shown in Table VIII) is surprising.

EXAMPLE 7

This example illustrates the difference in mildness between a commercially available acyl isethionate bar and acyl isethionate/cocamido MEA sulfosuccinate bars at different ratios of acyl isethionate to sulfosuccinate. Table X shows the formulations and Table XI gives Flex Wash results.

TABLE X

| Component | 15 | 16 | 17 |
|---|---|---|---|
| Sodium Cocoyl Isethionate | 33.10 | 43.9 | 43.7 |
| Stearic Acid | 29.80 | 20.1 | 23.9 |
| Sodium Isethionate | 9.10 | 11.0 | 13.8 |
| Disodium Cocamido MEA Sulfosuccinate | 15.00 | 15.2 | 12.0 |
| Water | 10.0 | 3.2 | 4.7 |
| Perfume | 1.0 | 1.0 | 1.0 |
| Sodium Chloride | 0.35 | 5.1 | 0.35 |
| Titanium Dioxide | 0.20 | 0.5 | 0.5 |
| Miscellaneous | 1.45 | — | — |
| Ratio Isethionate/Sulfosuccinate | 2.2/1 | 2.87/1 | 3.64/1 |

TABLE XI

| Formulation | Control | Mean Scores Endpoint Erythema | | Mean Rank Scores Erythema | | P-Value |
|---|---|---|---|---|---|---|
| | | Formulation | Control | Formulation | Control | |
| 15 | B | 0.794 | 1.735 | 10.79 | 24.21 | 0.0000 |
| 16 | B | 0.8 | 1.5 | 12.29 | 22.71 | 0.0018 |
| 17 | B | 0.9 | 1.6 | 12.56 | 22.44 | 0.0027 |

Formulations 15, 16, and 17 are shown to be significantly milder than B.

EXAMPLE 8

This example shows that the addition of small amounts of PEG-150, a polymer of ethylene oxide, or dextrin etc. does not deleteriously affect the mildness of sulfosuccinate, or betaine/isethionate toilet bars.

TABLE XII

| | % in Formulation (by Weight) | | |
|---|---|---|---|
| Component | 18 | 19 | 20 |
| Sodium Cocoyl Isethionate | 43.6 | 46.1 | 38.9 |
| Stearic Acid | 22.0 | 23.7 | 23.5 |
| Sodium Isethionate | 9.3 | 3.7 | 8.7 |
| Cocoamidopropyl Betaine | — | — | 5.9 |
| Disodium Cocamido MEA Sulfosuccinate | 15.2 | 9.0 | 10.0 |
| Sodium Chloride | 2.6 | 0.35 | 1.0 |
| PEG 150* | 1.0 | 1.0 | 3.0 |
| Dextrin | — | — | 10.0 |
| Water | 4.7 | 4.7 | 4.6 |
| Perfume | 1.0 | 1.0 | 1.0 |
| Titanium Dioxide | 0.5 | 0.5 | 0.5 |
| EHDP | 0.02 | 0.02 | 0.02 |
| EDTA | 0.02 | 0.02 | 0.02 |

*Carbowax 8000 (Union Carbide)

TABLE XIII

| Formulation | Control | Mean Scores Endpoint Erythema | | Mean Rank Scores Erythema | | P-Value |
|---|---|---|---|---|---|---|
| | | Formulation | Control | Formulation | Control | |
| 18 | B | 0.69 | 1.05 | 14.08 | 22.92 | 0.0096 |
| 19 | B | 0.8 | 1.27 | 15.69 | 21.31 | 0.1028 |
| 20 | B | 0.7 | 2.0 | 9.1 | 25.9 | 0.0000 |

Since the mildness of PEG-150 does not adversely affect the mildness of these formulations, this example also defines an acyl isethionate/sulfosuccinate ratio of 5/1 (formulation 19).

EXAMPLE 9

Lather Volume measurements and bar mush evaluations were performed on the forementioned formulations. The lather volume test is as described in Example 3 above and the mush test is as described briefly below.

Mush—Pre-weighed bars were immersed in water for 2 hours. The increase in weight was noted. Mush was removed and the remainder of the bar was dried. After re-weighing, mush was calculated as the weight of mush per 50 $cm^2$ of surface mushed. Lower values indicated better performance.

TABLE XIV

| Formulation # | Acyl Isethionate: Mono-Alkyl Sulfosuccinate | Lather Volume (ml) | Mush (g/50 $cm^2$) |
|---|---|---|---|
| 15 | 2.20:1 | 125 | — |
| 16 | 2.87:1 | 135 | 9.45 |
| 17 | 2.89:1 | 150 | 8.22 |
| 18 | 3.64:1 | 160 | 7.15 |
| 19 | 5.12:1 | 160 | 6.54 |
| Control Bar B | — | 150 | 8.25 |

All of the formulations in Table XIV have good to excellent lather and mush values comparable to the commercially available Control Bar B of Table I.

Examples 10–11 below relate to the embodiment of the invention comprising the combination of acyl isethionate, betaine and amido sulfosuccinate.

EXAMPLE 10

Three bars having compositions 20, 21 and 22 were tested for mildness against comparative bar B from Table I. The compositions of these bars are set forth below:

| Component | 20 | 21 | 22 |
|---|---|---|---|
| sodium cocoylisethionate | 47.0 | 47.0 | 47.0 |
| free fatty acid | 33.75 | 33.75 | 33.75 |
| sodium isethionate | 5.2 | 4.71 | 5.12 |
| disodium cocamido (HEA) sulfosuccinate | 6.0 | 1.0 | 3.5 |
| cocamidopropylbetaine | 1.0 | 6.0 | 3.5 |
| water | 5.0 | 5.0 | 5.0 |
| soap | — | — | — |
| LAS | — | — | — |
| perfume | 1.0 | 1.0 | 1.0 |
| sodium chloride | 0.5 | 1.0 | 0.59 |
| EHDP | 0.2 | 0.2 | 0.2 |
| EDTA | 0.2 | 0.2 | 0.2 |
| titanium dioxide | 0.5 | 0.5 | 0.5 |
| p value (versus IV) | 0.04 | 0.09 | 0.0007 |

As can be seen, each of bars 20–22 contain both amido sulfosuccinate and betmine and each bar was shown to be significantly milder than bar B. The very low p value for composition 22 suggests that mildness is even further improved as the ratio of these two coactives approaches 1 to 1.

EXAMPLE 11

The following two compositions 23 and 24 were tested for mildness against a commercially available bar Oil of Olay TM.

| Component | 23 | 24 |
|---|---|---|
| sodium cocoylisethionate | 50.0 | 48.8 |
| free fatty acid | 24.42 | 23.8 |
| sodium isethionate | 5.53 | 5.35 |
| disodium cocamido (MEA) sulfosuccinate | 6.0 | 6.0 |
| cocamidopropylbetaine | 2.0 | 2.0 |
| cetyl alcohol | 5.0 | 5.0 |

-continued

| Component | 23 | 24 |
|---|---|---|
| water | 5.0 | 5.0 |
| soap | — | 2.0 |
| perfume | 1.0 | 1.0 |
| sodium chloride | 0.5 | 1.0 |
| EHDP | 0.2 | 0.2 |
| EDTA | 0.2 | 0.2 |
| titanium dioxide | 0.5 | 0.5 |
| p value (versus Oil of Olay) | 0.002 | 0.04 | p Value for both bars show these bars to be significantly milder than Oil of Olay ™.

EXAMPLE 12

Two bars having compositions 25 and 26 were tested for mildness against comparative B from Table I. The composition of these bars are set forth below:

|  | 25 | 26 |
|---|---|---|
| Sodium Cocoyl Isethionate | 47.00 | 47.00 |
| Free Fatty Acid | 17.00 | 33.75 |
| Sodium Isethionate | 3.99 | 7.50 |
| Disodium cocamido (MEA) Sulfosuccinate | 11.75 | 2.35 |
| Cocamido Propylbetaine | 11.75 | 2.35 |
| Water | 5.00 | 5.00 |
| Soap | — | — |
| LAS | — | — |
| Perfume | 1.00 | 1.00 |
| Sodium Chloride | 1.96 | 0.50 |
| EHDP | 0.02 | 0.02 |
| EDTA | 0.02 | 0.02 |
| Titanium Dioxide | 0.50 | 0.50 |
| DEFI:Coactive Ratio | 2:1 | 10:1 |
| Flex Wash p value (versus Comparative B) | 0.0217 | 0.13 |

The example above shows that, even when the ratio of acyl isethionate to other coactives is 2:1 or 10:1, the bar compositions are significantly milder relative to the comparative bar. It should be noted that significance of composition 26 to Bar B is only at 87%, but this value may still be considered significant and certainly provides what is considered to be directional significance.

We claim:

1. A solid cleaning composition comprising:
   i) more than about 30% $C_{14}$ or lower acyl esters of isethionic acid salts, the acyl chain length distribution of said esters being at least about 95% $C_8$–$C_{18}$; and
   ii) at least one betaine wherein the weight ratio of said acyl esters to betaine is about 8:1 to about 2:1; and said betaine has the structure

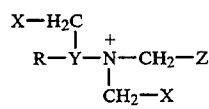

wherein, R is a hydrocarbon chain having a distribution of at least about 90% $C_5$–$C_{17}$;
   X is H, or $CH_2OH$;
   Y is methyl methylene or $CONHCH_2CH_2CH_2$;
   Z is $COO^-$, or $CHOHCH_2SO_3-$, provided that when X, Y and Z are respectively H, $CH_2$ and $COO^-$ in combination, R is less than 50% $C_{15}$–$C_{17}$; and
   iii) 0 to 10% soap.

2. A composition according to claim 1, wherein the ratio of isethionate ester to betaine is from 8:1 to 2:1.
3. A composition according to claim 1, wherein the length of said acyl chain has the following distribution:

| Chain Length | % |
|---|---|
| $C_{6-10}$ | 20–25 |
| $C_{12}$ | 45–55 |
| $C_{14-18}$ | 20–40 |
| $C_{18}$ unsaturated | 1–15. |

4. A skin cleansing toilet bar composition comprising:
   i) acyl esters of isethionic acid salts as defined in claim 1 in an amount of about 30% to 70%;
   ii) at least one betaine as defined in claim 1, wherein the weight ratio of said acyl esters to betaine is about 8:1 to about 2:1;
   iii) free fatty acid in an amount of 2–40%;
   iv) fatty alcohol in an amount of about 0–10%;
   v) sodium isethionate in an amount of 2–20%;
   vi) soap in an amount of about 0–10%; and
   vii) water in an amount of about 2–20%.
5. A composition according to claim 4, wherein the betaine is a carboxybetaine.
6. A composition according to claim 4, wherein the betaine is a sulfobetaine or hydroxy sultaine.
7. A composition according to claim 4, wherein the betaine is an amido betaine.
8. A composition according to claim 7, wherein the betaine is a cocamidopropyl betaine.
9. A skin cleansing composition comprising:
   i) more than about 30% $C_{14}$ or lower acyl esters of isethionic acid salts, the acyl chain length distribution of said esters being at least about 95% $C_8$–$C_{18}$; and
   ii) at least one amido sulfosuccinate wherein the weight ratio of said acyl esters to sulfosuccinate is about 6:1 to about 2:1.
10. A composition according to claim 9, wherein the amido sulfosuccinate is a mono ester.
11. A composition according to claim 9, wherein the amido sulfosuccinate is derived from a monoethanolamide.
12. A composition according to claim 9, wherein the amido sulfosuccinate is a cocamido sulfosuccinate.
13. A composition according to claim 9, wherein the ratio of isethionate ester to amido sulfosuccinate is from 4.5:1 to 3:1.
14. A composition according to claim 9, wherein said acyl chain length has the following distribution:

| Chain Length | % |
|---|---|
| $C_{6-10}$ | 10–25 |
| $C_{12}$ | 45–55 |
| $C_{14-18}$ | 20–40 |
| $C_{18}$ unsatured | 1–15. |

15. A solid skin cleansing composition comprising:
   (i) about 30–70% by wt. acyl esters of isethionic acid salts wherein more than about 30% of said acyl esters are $C_{14}$ or lower and wherein the acyl chain length distribution of said acyl esters is at least about 95% $C_8$ to $C_{18}$;

(ii) at least one amido sulfosuccinate wherein the weight ratio of said acyl esters to sulfosuccinate is about 6:1 to 2:1;
(iii) free fatty acid in an amount of about 2-40%;
(iv) fatty alcohol in an amount about 0-10%;
(v) sodium isethionate in an amount of about 2-20%;
(vi) soap in an amount of about 0-10%; and
(vii) water in an amount of about 2-20%.

16. A skin cleansing composition comprising:
(i) more than about 30% $C_{14}$ or lower acyl esters of isethionic acid salts, the acyl chain length distribution of said esters being at least 95% $C_8$-$C_{18}$;
(ii) at least one betaine having the structure

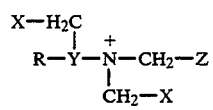

wherein, R is a hydrocarbon chain having a distribution of at least about 90% $C_5$-$C_{17}$;
X is H, or $CH_2OH$;
Y is methyl methylene or $CONHCH_2CH_2CH_2$;
Z is $COO^-$, or $CHOHCH_2SO_3-$, provided that when X, Y and Z are respectively H, $CH_2$ and $COO^-$ in combination, R is less than 50% $C_{15}$-$C_{17}$;
in an amount from about 0.5 to 7.5% by weight of the composition;
(iii) at least one amido sulfosuccinate in an amount about 1-24% by weight of the composition;
wherein ratio of isethionate to total coactive is from about 10:1 to 2:1.

17. A composition according to claim 16, wherein said acyl chain length has the following distribution:

| Chain Length | % |
| --- | --- |
| $C_{6-10}$ | 10-25 |
| $C_{12}$ | 45-55 |
| $C_{14-16}$ | 20-40 |
| $C_{18}$ unsatured | 1-15. |

18. A composition according to claim 16, wherein the betaine is carboxybetaine.

19. A composition according to claim 16, wherein the betaine is sulfobetaine or hydroxy sultaine.

20. A composition according to claim 16, wherein the betaine is an amido betaine.

21. A composition according to claim 16, wherein the betaine is cocamidopropyl betaine.

22. A composition according to claim 16, wherein the amido sulfosuccinate is a monoester.

23. A composition according to claim 16, wherein the amido sulfosuccinate is derived from monoethanolamide.

24. A composition according to claim 16, wherein the sulfosuccinate is a cocamido sulfosuccinate.

25. A skin cleansing composition comprising:
i) more than about 30% $C_{14}$ or lower acyl esters of isethionic acid salts, the acyl chain length distribution of said esters being at least about 95% $C_8$-$C_{18}$; and
ii) at least one betaine wherein the weight ratio of said acyl esters to betaine is about 8:1 to about 2:1; and said betaine has the structure

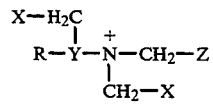

wherein, R is a hydrocarbon chain having a distribution of at least about 90% $C_5$-$C_{17}$;
X is H, or $CH_2OH$;
Y is methyl methylene or $CONHCH_2CH_2CH_2$;
Z is $COO^-$, or $CHOHCH_2SO_3-$, provided that when X, Y and Z are respectively H, $CH_2$ and $COO^-$ in combination, R is less than 50% $C_{15}$-$C_{17}$; and
(iii) at least one amido sulfosuccinate;
(iv) free fatty acid in an amount of about 2-40%;
(v) fatty alcohol in an amount of about 0-10%;
(vi) sodium isethionate in an amount of about 2-20%;
(vii) soap in an amount of about 0-10%; and
(viii) water in an amount of about 2-20%.

26. A composition according to claim 25, wherein the sulfosuccinate is amido sulfosuccinate.

* * * * *